(12) United States Patent
Wang et al.

(10) Patent No.: US 8,579,819 B2
(45) Date of Patent: Nov. 12, 2013

(54) BREAST ULTRASOUND SCANNING TEMPLATE

(75) Inventors: Shih-Ping Wang, Los Altos, CA (US); Jiayu Chen, Palo Alto, CA (US); Douglas G. Summers, Palo Alto, CA (US)

(73) Assignee: Shih-Ping Bob Wang, Los Altos, CA (US)

( * ) Notice: Subject to any disclaimer, the term of this patent is extended or adjusted under 35 U.S.C. 154(b) by 0 days.

(21) Appl. No.: 13/296,023

(22) Filed: Nov. 14, 2011

(65) Prior Publication Data

US 2012/0089026 A1    Apr. 12, 2012

Related U.S. Application Data

(63) Continuation of application No. 11/513,481, filed on Aug. 30, 2006, now abandoned.

(60) Provisional application No. 60/713,282, filed on Sep. 1, 2005.

(51) Int. Cl.
*A61B 8/00* (2006.01)

(52) U.S. Cl.
USPC .......................................................... 600/443

(58) Field of Classification Search
USPC .......................................................... 600/443
See application file for complete search history.

(56) References Cited

U.S. PATENT DOCUMENTS

| | | | |
|---|---|---|---|
| 4,338,948 A | 7/1982 | Perez-Mendez et al. | |
| 4,886,494 A | 12/1989 | Morifuji | |
| 6,304,770 B1 * | 10/2001 | Lee et al. | 600/427 |
| 6,475,150 B2 | 11/2002 | Haddad | |
| 6,504,157 B2 | 1/2003 | Juhi | |
| 2003/0007598 A1 | 1/2003 | Wang et al. | |
| 2003/0167004 A1 | 9/2003 | Dines et al. | |
| 2003/0181801 A1 | 9/2003 | Lasser et al. | |
| 2003/0233110 A1 * | 12/2003 | Jesseph | 606/167 |
| 2004/0030255 A1 | 2/2004 | Alfano et al. | |
| 2004/0215101 A1 | 10/2004 | Rioux et al. | |
| 2006/0020279 A1 | 1/2006 | Chauhan et al. | |

FOREIGN PATENT DOCUMENTS

| WO | WO03103500 A1 | 12/2003 |
|---|---|---|
| WO | WO2004/030523 A2 | 4/2004 |
| WO | WO2005/104729 A2 | 10/2005 |

\* cited by examiner

*Primary Examiner* — Tse Chen
*Assistant Examiner* — Hien Nguyen
(74) *Attorney, Agent, or Firm* — Cooper & Dunham LLP

(57) ABSTRACT

Apparatus and related methods for facilitating volumetric ultrasonic scanning of a breast are described. In one preferred embodiment, a generally cone-shaped radial scanning template having a vertex and a wide opening angle is provided, the radial scanning template having a slot-like opening extending outward from the vertex through which an ultrasound transducer scans the breast as the radial scanning template is rotated. In another preferred embodiment, a flexible membrane for compressing a skin surface of the breast is provided, the flexible membrane being mounted on a mechanical assembly such as a roller assembly to form a slot-like opening through which an ultrasound transducer directly contacts the skin surface, the flexible membrane rising and falling relative to the skin surface but not moving laterally as the slot-like opening and ultrasound transducer move laterally across the compressed breast, whereby stabilization of the breast and direct transducer-skin contact are concurrently achieved.

5 Claims, 11 Drawing Sheets

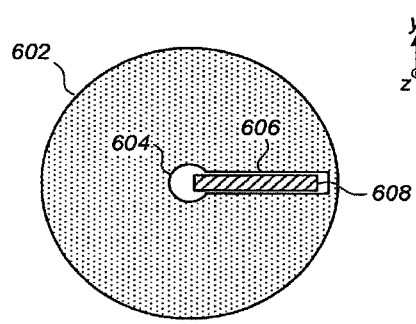
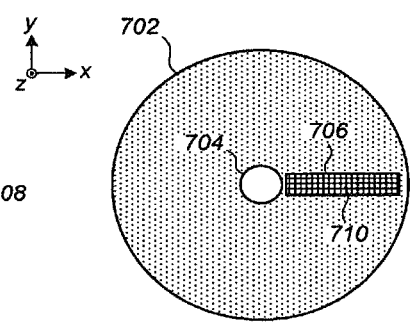
FIG. 6    FIG. 7
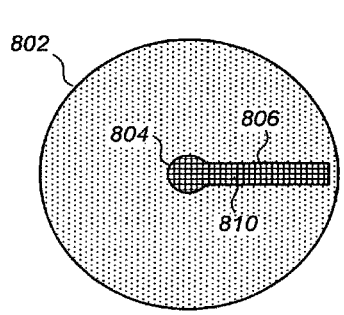
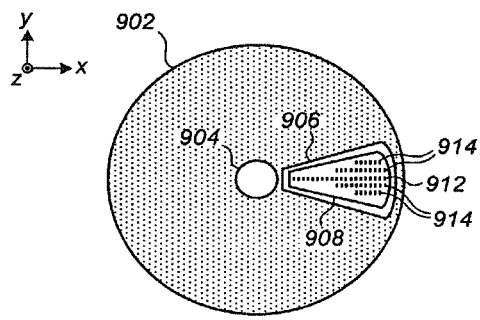
FIG. 8    FIG. 9

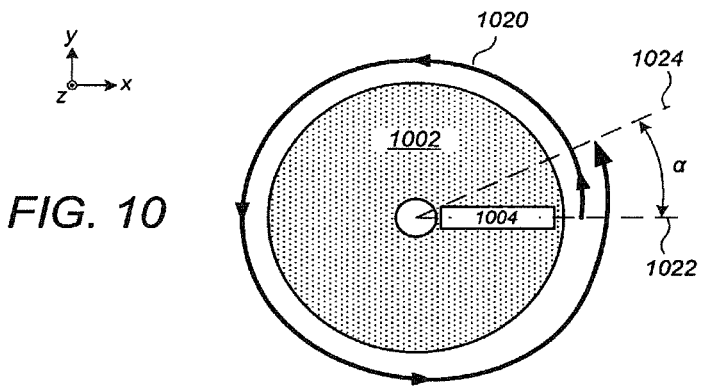
FIG. 10
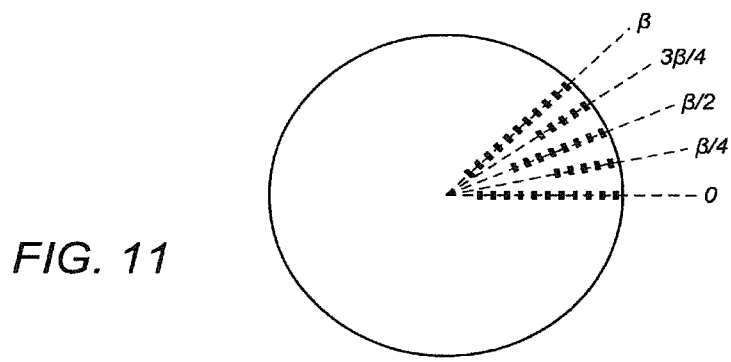
FIG. 11
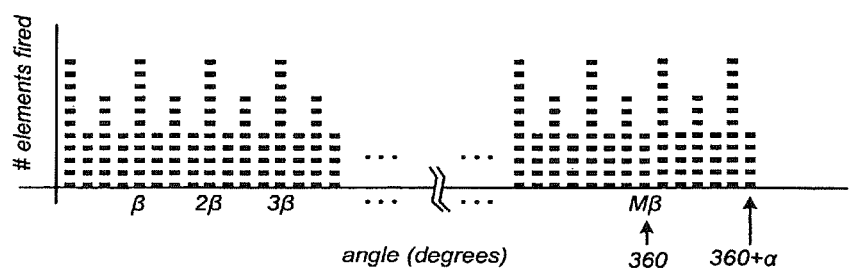

BREAST ULTRASOUND SCANNING TEMPLATE

CROSS-REFERENCE TO RELATED APPLICATIONS

This application is a Rule 1.53(b) continuation of U.S. patent application Ser. No. 11/513,481, filed Aug. 30, 2006, which in turn claims benefit of U.S. Provisional Application No. 60/713,282, filed Sep. 11, 2005.

TECHNICAL FIELD

This patent specification relates to medical imaging. More particularly, this patent specification relates to breast ultrasound scanning

BACKGROUND

Volumetric ultrasound scanning usually involves the movement of an ultrasound transducer relative to a tissue sample and the processing of resultant ultrasound echoes to form a data volume representing at least one acoustic property of the tissue sample. Volumetric ultrasound scanning of the breast has been proposed as a complementary modality for breast cancer screening as described, for example, in the commonly assigned US 2003/007598A1, which is incorporated by reference herein. The commonly assigned WO 2004/030523A2, which is incorporated by reference herein, describes a full-field breast ultrasound (FFBU) scanning apparatus that compresses a breast along planes such as the craniocaudal (CC) plane, the mediolateral oblique (MLO) plane, etc., and ultrasonically scans the breast. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast.

Other FFBU scanning devices that compress the breast in other directions, such as in generally chestward or "head-on" directions, are described in one or more of the following commonly assigned applications, each of which is incorporated by reference herein: U.S. Ser. No. 60/565,698 filed Apr. 26, 2004; U.S. Ser. No. 60/577,078 filed Jun. 4, 2004; U.S. Ser. No. 60/629,007 filed Nov. 17, 2004; WO 2005/104573 A2; and WO 2005/120357 A1. It would be desirable to facilitate ultrasound scanning of a breast in a manner that promotes volumetric completeness and good image quality while also promoting patient comfort and clinical efficiency.

WO 03/103500 discusses the use of a tissue molding element having a hole through which an ultrasonic transducer scans the breast as the tissue molding element is rotated. However, in comparison to one or more of the preferred embodiments described herein, the device(s) discussed in WO 03/103500 bring about one or more shortcomings in relation to volumetric completeness, image quality, patient comfort, and/or clinical efficiency. Other issues arise as would be readily apparent to one skilled in the art in view of the present disclosure.

SUMMARY

An apparatus and related methods for ultrasonically scanning a tissue sample are provided, the apparatus comprising an ultrasound transducer and a radial scanning template that compresses the breast in a generally chestward direction, the radial scanning template being generally cone-shaped and having a vertex and an opening angle. The radial scanning template has a slot-like opening extending outward from the vertex through which the ultrasound transducer scans the breast as the radial scanning template is rotated. According to one preferred embodiment, the opening angle is substantially greater than ninety degrees. In another preferred embodiment, the opening angle is greater than 120 degrees, and in still another preferred embodiment, the opening angle is greater than 135 degrees.

Generally speaking, a wider opening angle substantially greater than 90 degrees promotes improved flattening of the breast tissue toward the chest wall, thereby reducing the required scan depth. This allows for higher ultrasound scan frequencies to be used (e.g., 10 MHz-15 MHz) which, in turn, results in improved image quality. The described radial scanning template is particularly effective for ultrasonically scanning the breast of a supine patient, although application to other patient positions (e.g., prone, upright) is within the scope of the preferred embodiments.

In one preferred embodiment, the center of rotation of the radial scanning template is located at the vertex, and the vertex is positioned atop the breast nipple. Optionally, a central opening is provided that receives the nipple of the breast such that the nipple surface is not compressed to the same extent as the remainder of the skin surface.

Preferably, the radial scanning template comprises a material that is semi-rigid, or substantially rigid, and that is optically translucent for facilitating breast positioning and scanning. In one preferred embodiment, the ultrasound transducer directly contacts a skin surface of the breast while scanning the breast through the slot-like opening. In another preferred embodiment, a membrane extends across the slot-like opening, and the ultrasound transducer scans the breast through the membrane. The membrane may comprise a thin film sheet, such as Mylar or Melinex, that is nonporous to ultrasound coupling agent. Alternatively, the membrane may comprise a fabric material porous to ultrasound coupling agent.

According to one preferred embodiment, there is only a single ultrasound transducer and only a single slot-like opening in the radial scanning template. The radial scanning template is rotated by 360 degrees plus an overlap angle during the breast ultrasound scan, the overlap angle being in a range of 5 to 45 degrees. Thus, breast tissue within the overlap angle is scanned twice. The dual scans can be used to reduce a discontinuity in the resulting volumetric representation of the breast associated with the start-stop location of the radial scan.

According to another preferred embodiment, a plurality of ultrasound transducers and a corresponding plurality of slot-like openings are provided. In general, where there are N transducers, a full volumetric scan can be achieved by rotating the radial scanning template by 360/N degrees, plus an overlap angle if desired.

In one preferred embodiment, at least two of the ultrasound transducers have different lengths corresponding to different vertex-to-base distances around the radial scanning template. Each ultrasound transducer scans a different coronal sector of the breast. In one example, a longer of the ultrasound transducers can be responsible for the coronal sector of the breast that is nearest the axilla, which usually extends farther out from the nipple than other sectors. In another preferred embodiment, one or more of the ultrasound transducers can be tilted at different angles from a normal to the coronal plane for facilitating tilt-based compounding and/or volumetric completeness of the scan.

In other preferred embodiments, various parameters associated with the multiple ultrasound transducers can be varied, and the resulting scans can be compounded in various advantageous ways. Examples of parameters that can be varied among different transducers includes, but is not limited to, scan frequency, tilt angle, elevation beamwidth, scan mode (e.g., B-mode, harmonic, Doppler), in-plane acoustic interrogation angles, and different in-plane multi-angle compounding schemes.

In one preferred embodiment, a scanning surface of an ultrasound transducer has fewer rows of transducer elements nearer the vertex and more rows of transducer elements farther from the vertex. This can promote more uniform voxel elements in the volumetric ultrasound scan and faster scanning intervals. In another preferred embodiment, the ultrasound transducer comprises a single linear array of transducer elements, but different subsets of the transducer elements are fired at different rotational positions, with transducer elements farther from the vertex being fired at more rotational positions than transducer elements nearer to the vertex. This can likewise promote more uniform voxel elements in the volumetric ultrasound scan and faster scanning intervals.

In one preferred embodiment, the slot-like opening and the ultrasound transducer both extend along substantially all of a vertex-to-base length of the radial scanning template, such that a complete volumetric scan can be achieved in a single 360-degree rotation. In another preferred embodiment, the ultrasound transducer extends only along a portion of the slot-like opening and is slidably translated along the slot-like opening during multiple rotations of the radial scanning template for achieving volumetric completeness of the scan.

In another preferred embodiment, an apparatus for ultrasonically scanning a breast is provided, comprising a plurality of ultrasound transducers and a scanning template comprising a generally cone-shaped surface that compresses the breast in a generally chestward direction. The generally cone-shaped surface has a vertex and defines a plurality of slot-like openings extending outward from the vertex through which the plurality of ultrasound transducers, respectively, scan the breast as the scanning template is rotated.

In another preferred embodiment, an apparatus for ultrasonically scanning a breast is provided, comprising an ultrasound transducer having a scanning surface, and a compressor having a compressive surface that compresses a skin surface of the breast, wherein a slot-like opening is formed in the compressive surface through which the scanning surface of the ultrasound transducer directly contacts the skin surface. The compressor is configured such that the slot-like opening moves laterally over the compressed skin surface in conjunction with the ultrasound transducer as the ultrasound transducer is moved thereacross to ultrasonically scan the breast. Thus, both breast compression and direct skin contact are advantageously provided during the ultrasound scan. In one example, the compressive surface comprises a flexible membrane and a roller assembly causing the membrane to rise and fall relative to the skin surface, but not to move laterally relative to the skin surface, as the ultrasound transducer is moved laterally across the compressed breast. In one preferred embodiment, the membrane comprises a thin film sheet that is nonporous to ultrasound coupling agent, while in another

BRIEF DESCRIPTION OF THE DRAWINGS

The above mentioned and other aspects, features and advantages can be more readily understood from the following detailed description with reference to the accompanying drawings wherein:

FIG. 6 illustrates a top view of a radial scanning template 602 according to a preferred embodiment;

FIG. 7 illustrates a top view of a radial scanning template 702 according to a preferred embodiment;

FIG. 8 illustrates a top view of a radial scanning template 802 according to a preferred embodiment;

FIG. 9 illustrates a top view of a radial scanning template 902 according to a preferred embodiment;

FIG. 10 illustrates a top view of a radial scanning template 1002 according to a preferred embodiment;

FIG. 11 illustrates a conceptual example of a 1D ultrasound transducer firing scheme according to a preferred embodiment;

DETAILED DESCRIPTION

Figure 1:
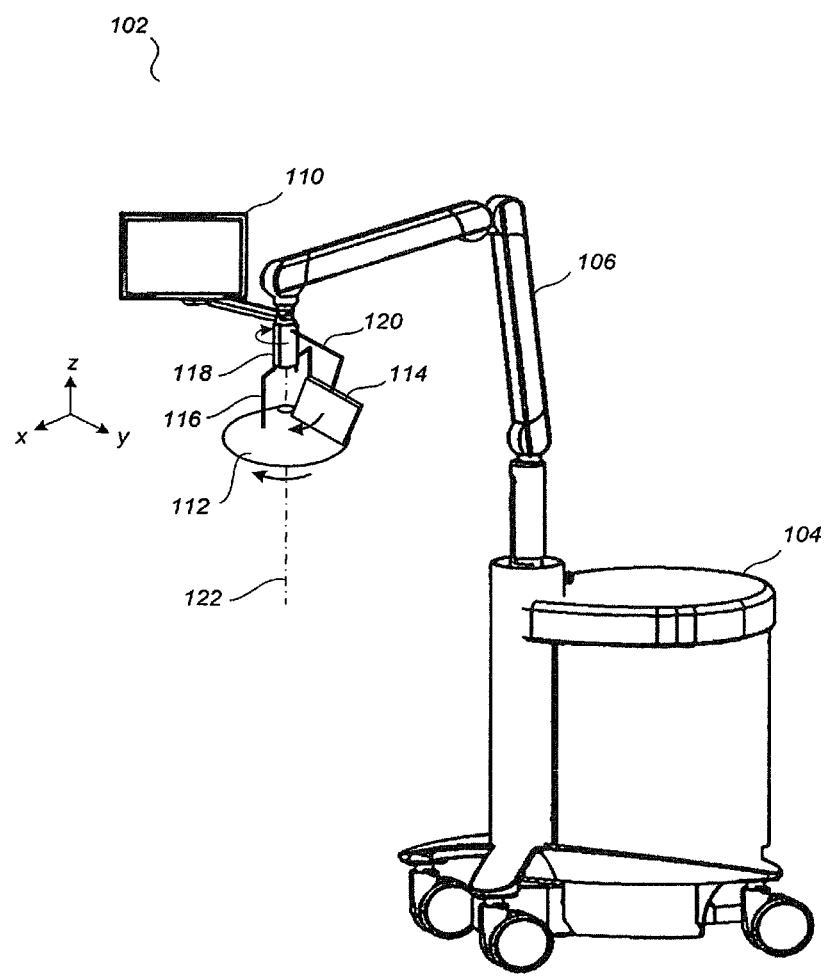
FIG. 1 illustrates a perspective view of a full-field breast ultrasound (FFBU) scanning apparatus 102 according to a preferred embodiment.

FIG. 1 illustrates a perspective view of a full-field breast ultrasound (FFBU) scanning apparatus 102 according to a preferred embodiment, comprising a frame 104 that may contain an ultrasound processor, a movable support arm 106, and a monitor 110 connected to the support arm 106. FFBU scanning apparatus 102 further comprises a radial scanning template 112 and an ultrasound transducer 114. The radial scanning template 112 downwardly compresses a breast of a supine patient while rotating around an axis 122. The ultrasound transducer 114 rotates with the radial scanning template 112 and scans the breast through a slot-like opening therein. For reference purposes herein, the +z direction refers to an outward direction away from the chest wall, the x-axis refers to a left-right direction, and the y-axis refers to a head-to-toe direction. The x-y plane thus corresponds to a coronal plane, the x-z plane corresponds to an axial plane, and the y-z plane corresponds to a sagittal plane.

Also shown in FIG. 1 is a rigid two-pronged connector 116 and a rigid single-armed connector 120 that mechanically connect the radial scanning template 112 and the ultrasound transducer 114, respectively, to an actuator assembly 118 for achieving the movement functionalities described herein. It is to be appreciated that the mechanical elements 116-120 in FIG. 1 are drawn by way of conceptual example only. In view of the present disclosure, a person skilled in the art would be readily able to construct the various mechanical linkages, actuators, motors, sensors, etc., required to achieve the described mechanical functionalities without undue experimentation. Accordingly, such mechanical details are mostly omitted from the drawings herein for clarity of description.

Preferably, the support arm 106 is configured and adapted such that the overall compression/scanning assembly 112-120 is either (i) neutrally buoyant in space, or (ii) has a light net downward weight (e.g., 2-3 pounds) for breast compression, while allowing for easy user manipulation. Optionally, the support arm 106 may comprise potentiometers (not shown) to allow position and orientation sensing for the overall compression/scanning assembly 112-120, or other types of position and orientation sensing (e.g., gyroscopic, magnetic, optical, radio frequency (RF)) can be used.

Within frame 104 may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

Figure 2:
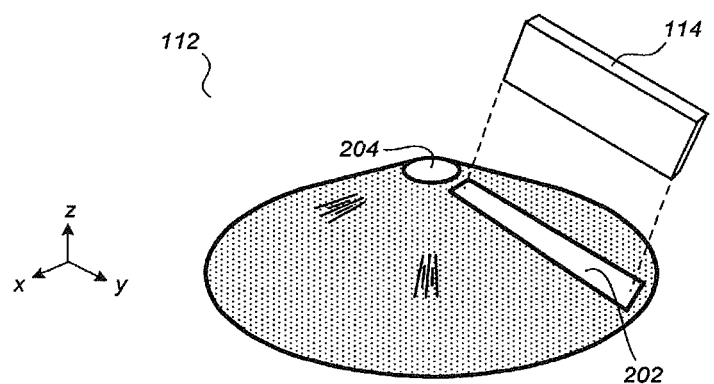
FIGS. 2-3 illustrate more detailed views of the radial scanning template 112 in accordance with a preferred embodiment.
Figure 3:
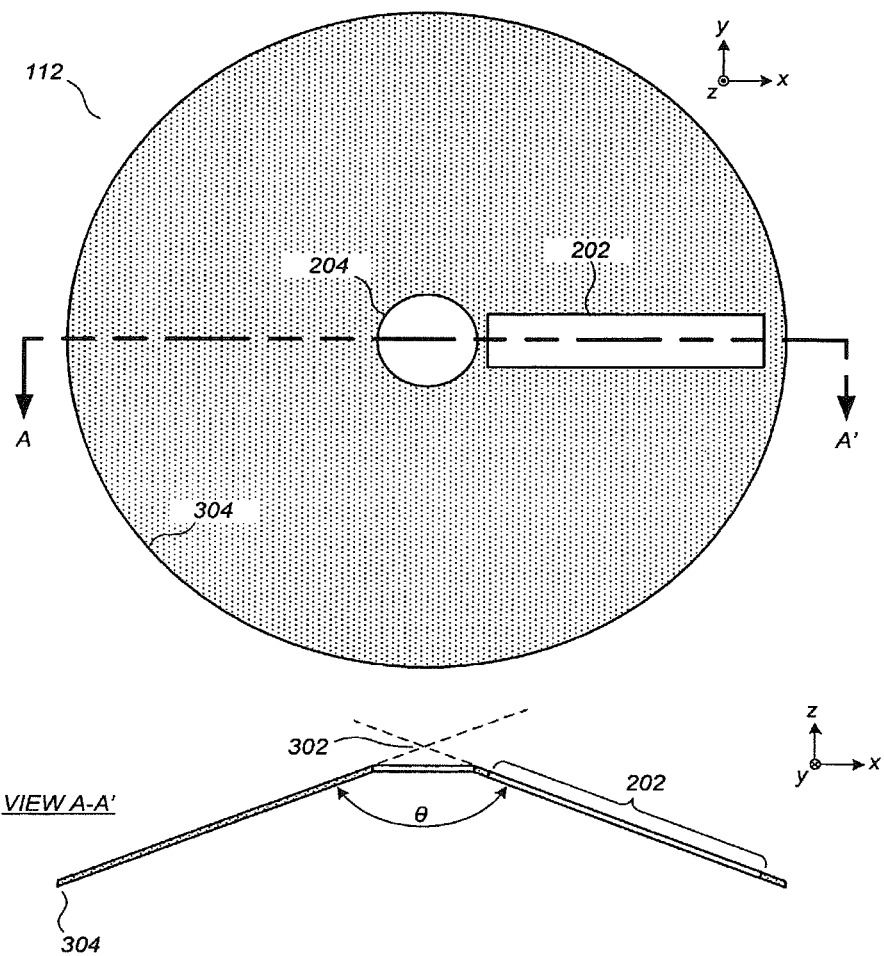

FIGS. 2-3 illustrate more detailed views of the radial scanning template 112 in accordance with a preferred embodiment. Radial scanning template 112 has a generally conical shape and defines therein a slot-like opening 202 and a central opening 204. The slot-like opening 202 is dimensioned to allow the ultrasound transducer 114 to at least partially pass therethrough to scan the breast. Although shown as a 1D array in FIG. 2, the ultrasound transducer 114 may more generally be 1D, 1.25D, 1.5D, 2D, or hybridization thereof without departing from the scope of the preferred embodiments. In one preferred embodiment, the FFBU scanning apparatus 102 is provided with an interchangeable (and/or disposable) set of radial scanning templates 112 that are differently sized for differently-sized breasts. In one example, three (3) different radial scanning templates having base diameters of 6 inches, 8 inches, and 10 inches are provided. Exemplary diameters for the central opening 204 range between about 0.25" to 1.5". The slot-like opening 202 may have a width in the range of 0.25" to 1" depending on the size of the ultrasound transducer to be inserted therethrough.

In one preferred embodiment, the ultrasound transducer 114 is supported and actuated independently from the radial scanning template 112. In another preferred embodiment, the ultrasound transducer 114 is integral with, clipped to, or otherwise fused with the radial scanning template 112 for joint support and/or actuation.

With reference to FIG. 3 at view A-A', the radial scanning template 112 is shaped similarly to a cone having a vertex 302, a base 304, and an opening angle θ. In one preferred embodiment, the opening angle θ is greater than 90 degrees and less than 175 degrees. In another preferred embodiment, the opening angle θ is greater than 120 degrees and less than 165 degrees. In yet another preferred embodiment, the opening angle θ is greater than 135 degrees and less than 155 degrees. In general, the opening angle θ should be large enough to provide sufficiently flat chestward compression, while not being so large as to "lose control" of the lateral position of the breast during positioning or rotation.

In one preferred embodiment, the radial scanning template 112 is formed from a translucent, semi-rigid material having mechanical properties similar to those of 40-mil polycarbonate plastic, 40-mil polystyrene plastic, or an equivalent amount of polyethylene terephthalate (PETE) plastic. In this embodiment, there is some amount of "give" or flexibility to the template 102 providing at least some degree of comfort to the patient as well as adaptability to differently-shaped breasts, while at the same time providing for substantial stabilization of the breast tissue for reliable volumetric imaging of the breast. In another preferred embodiment, the material for template 102 comprises a translucent, substantially rigid material such as 140-mil glass, 140-mil acrylic, or 140-mil polycarbonate plastic. Preferably, a lower surface of the radial scanning template 112 makes a slippery contact with the skin surface in the presence of an ultrasound couplant so that rotation is easily achieved even when the breast is under some degree (e.g., 4-12 lbs.) of downward compression. Despite the slippery contact with the breast, stabilization is provided by virtue of the generally conical shape of the radial scanning template 112. Preferably, a curled lip (not shown) is provided around the base 304 to prevent skin cuts, similar to the way curled upper lips are provided on many polystyrene and PETE plastic drinking cups.

Figure 4A:
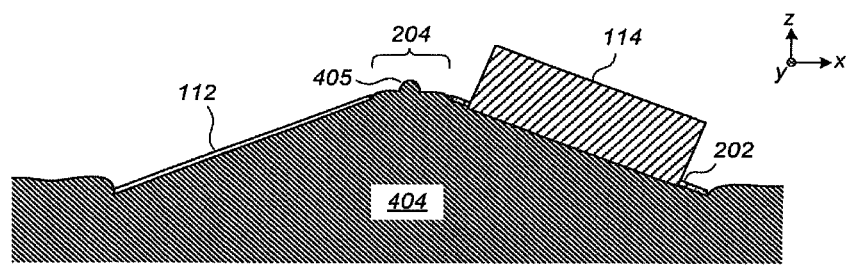
FIG. 4A illustrates a side cut-away view of the radial scanning template 112 as it chestwardly compresses a breast 404 having a nipple 405.
Figure 4B:
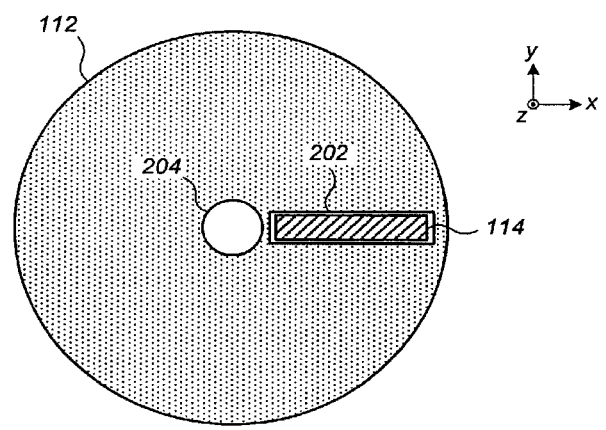
FIG. 4B illustrates a top conceptual view of FIG. 4A.

FIG. 4A illustrates a side cut-away view of the radial scanning template 112 as it chestwardly compresses a breast 404 having a nipple 405. The nipple 405 protrudes through the central opening 204. The transducer 114 scans the breast 404 through the slot-like opening 202. FIG. 4B illustrates a top conceptual view of FIG. 4A.

Figure 5A:
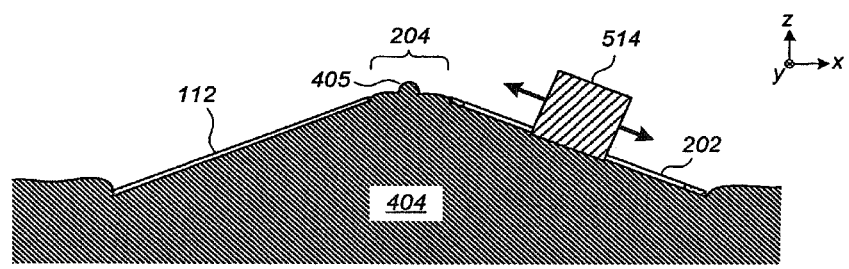
FIGS. 5A-5B illustrate a scenario according to another preferred embodiment in which the slot-like opening 202 extends along substantially all of a vertex-to-base length of the radial scanning template, but in which an ultrasound transducer 514 extends only along a portion of the slot-like opening.
Figure 5B:
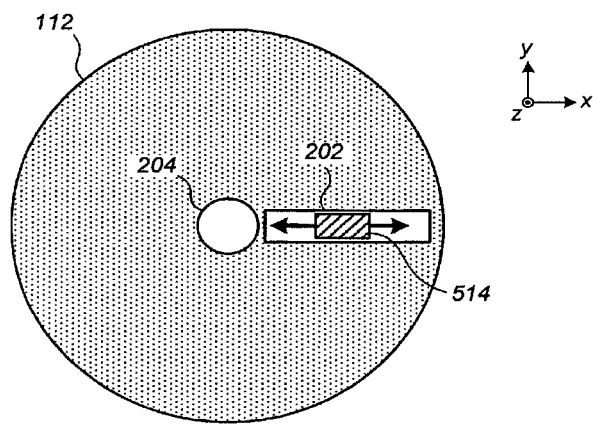

In the particular embodiment of FIGS. 4A and 4B, the slot-like opening 202 and the ultrasound transducer 114 both extend along substantially all of a vertex-to-base length of the radial scanning template such that a complete volumetric scan can achieved in a single 360-degree rotation (optionally using beamsteering for facilitating sub-areola imaging). In contrast, FIGS. 5A-5B illustrate a scenario according to another preferred embodiment in which the slot-like opening 202 extends along substantially all of a vertex-to-base length of the radial scanning template, but in which an ultrasound transducer 514 extends only along a portion of the slot-like opening. In this preferred embodiment, the ultrasound transducer 514 is slidably translated along the slot-like opening 202 during multiple rotations of the radial scanning template 112 for achieving volumetric completeness.

FIG. 6 illustrates a top view of a radial scanning template 602 according to a preferred embodiment, comprising a central opening 604 that is contiguous with a slot-like opening 606. An ultrasound transducer 608 can then extend farther inward toward the axis of rotation for better sub-areola imaging.

FIG. 7 illustrates a top view of a radial scanning template 702 according to a preferred embodiment, comprising a central opening 704, a slot-like opening 706, and a membrane 710 extending across the slot-like opening 706. The ultrasound transducer (not shown) scans the breast through the membrane 710.

In one preferred embodiment, the membrane 710 comprises a thin film sheet, such as Mylar or Melinex, that is nonporous to ultrasound coupling agent. In another preferred embodiment, the membrane can be vented (e.g., punctured or stamped with a pattern of small holes) for allowing porosity relative to the coupling agent, which can be advantageous in that air bubbles are reduced. Examples of other materials that can be used for the vented or non-vented membrane include, but are not limited to, polypropylene, polyester, polyethylene, PTFE, PET, paper, Kevlar, metal, and epoxy-fiber composite materials.

In another preferred embodiment, the membrane 710 comprises a fabric material porous to ultrasound coupling agent, which can be advantageous in that air bubbles are reduced. As used herein, fabric refers generally to a material structure of interconnected parts, such as can be formed by knitting, weaving, or felting natural or synthetic fibers, assembling natural or synthetic fibers together into an interlocking arrangement, fusing thermoplastic fibers, or bonding natural or synthetic fibers together with a cementing medium, and further refers to materials having similar textures or qualities as those formed thereby, such as animal membranes or other naturally occurring substances having fabric-like properties (either inherently or by processing), and such as materials generated by chemical processes yielding fabric-like webbings. One particularly suitable material for the taut fabric sheet comprises a polyester organza material having a filament diameter of about 40 microns and a filament spacing of about 500 microns. However, the fabric membrane may comprise any of a variety of other fabrics that are substantially inelastic and generally porous to ultrasound couplants without departing from the scope of the present teachings. Examples include, but are not limited to, polyester chiffon fabrics and cloth fabrics comprising straight weaves of substantially inelastic fibers. Where the weave is particularly tight (for example, the cloth used in men's dress shirts or the cloth used in many bed sheets), porosity can be achieved by perforating the cloth or otherwise introducing irregularities that allow the ultrasound couplant to soak or seep through.

FIG. 8 illustrates a top view of a radial scanning template 802 according to a preferred embodiment. In this preferred embodiment, a membrane 810 extends across the contiguous combination of a central opening 804 and a slot-like opening 806, whereby an ultrasound transducer (not shown) can then extend farther inward toward the axis of rotation for better sub-areola imaging through the membrane 810.

FIG. 9 illustrates a top view of a radial scanning template 902 according to a preferred embodiment, comprising a central opening 904 and a slot-like opening 906, the slot-like opening 906 being sector-shaped or "pie-shaped". An ultrasound transducer 908 is also sector-shaped and comprises, in addition to a full single row of transducer elements 912, additional transducer elements 914 formed in partial rows having greater numbers of elements toward a periphery of the device than toward the center. Where a conventional 1D probe is used in a conventional manner during the scanning rotation, a problem arises in that the scanning is more dense (greater number of voxels per unit volume) near the center while being less dense (lesser number of voxels per unit volume) near the periphery. In such conventional scenario, scanning is unnecessarily slow because of oversampling near the center of the volume, which is a necessary by-product of achieving sufficient sampling at the periphery. In contrast, using the preferred embodiment of FIG. 9, there is a more uniform scanning distribution. The scanning interval can be faster because oversampling near the center of the volume is avoided.

FIG. 10 illustrates a top view of a radial scanning template 1002 according to a preferred embodiment, comprising a single slot-like opening 1004 corresponding to a single ultrasound transducer (not shown). The radial scanning template is preferably rotated by 360 degrees plus an overlap angle a during the breast ultrasound scan, the overlap angle $\alpha$ being in a range of 5 to 45 degrees. The coronal sector associated with the overlap angle $\alpha$ (i.e., the pie-shaped sector of the compressed breast subtending the arc between radial lines 1022 and 1024 in FIG. 10) is thus imaged twice. The dual volumetric images for the overlap sector can be advantageously used to reduce discontinuity artifacts in the volumetric representation of the breast that might otherwise occur along the radial line 1022. In one preferred embodiment, the dual volumetric images are arithmetically averaged for smoothing over the discontinuity. Any of a variety of other mathematical methods for processing the dual volumetric images for reducing discontinuity artifacts are within the scope of the preferred embodiments.

FIG. 11 illustrates a conceptual example of a 1D ultrasound transducer firing scheme according to a preferred embodiment. For a particular coronal sector subtending a repeating unit interval $\beta$ (which may be, for example, 2-10 degrees but exaggerated at 45 degrees for the purposes of FIG. 11), different combinations of transducer elements are fired as the 1D ultrasound transducer is rotated. More particularly, transducer elements closer to the periphery are fired more often (i.e., at more rotational positions) than transducer elements closer to the vertex. For reasons similar to those presented supra in relation to FIG. 9, a more uniform voxel distribution and faster scanning intervals are facilitated.

Figure 12:
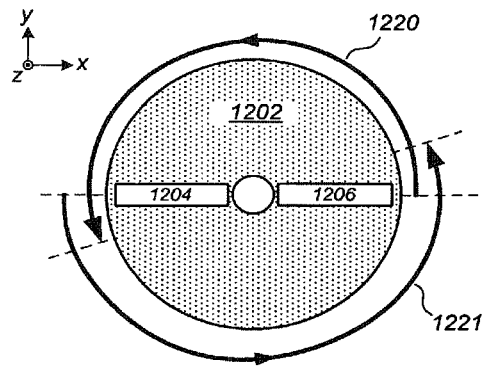
FIG. 12 illustrates a top view of a radial scanning template 1202 according to a preferred embodiment.

FIG. 12 illustrates a top view of a radial scanning template 1202 according to a preferred embodiment, comprising two slot-like openings 1204 and 1206 corresponding to two ultrasound transducers (not shown). In one preferred embodiment, the radial scanning template 1202 is preferably rotated by 180 degrees plus an overlap angle during the breast ultrasound scan, thereby reducing scanning time as compared to the use of a single ultrasound transducer.

In another preferred embodiment, the radial scanning template 1202 is rotated by the full 360 degrees plus overlap angle, with the different ultrasound transducers being differently configured with respect to at least one imaging parameter. The resultant volumetric scans are then compounded in any of a variety of advantageous ways. Parameters that may be varied among the transducers include, but are not limited to, scan frequency, tilt angle, elevation beamwidth, scan mode (e.g., B-mode, harmonic, Doppler), in-plane acoustic interrogation angles, and different in-plane multi-angle compounding schemes.

Figure 13:
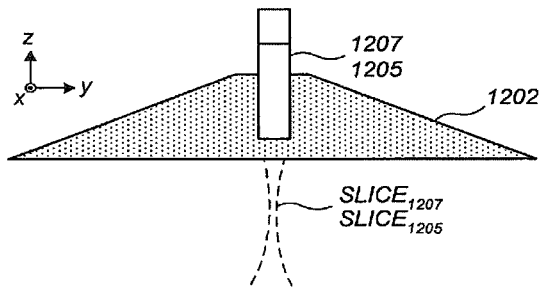
FIGS. 13-14 illustrate side perspective views of the radial scanning template 1202 as used in conjunction a first ultrasound transducer 1207 according to an embodiment.
Figure 14:
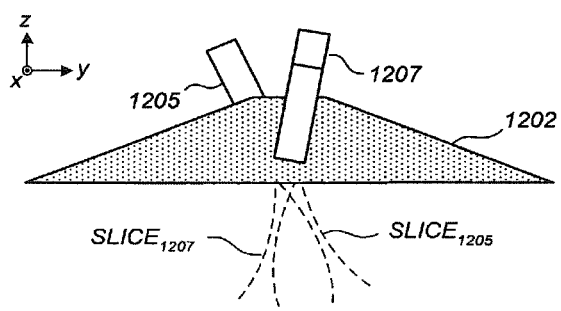

FIGS. 13-14 illustrate side perspective views of the radial scanning template 1202 as used in conjunction a first ultrasound transducer 1207 that scans through slot-like opening 1206 and a second ultrasound transducer 1205 that scans through slot-like opening 1204, as viewed from the +x direction. FIG. 13 illustrates the ultrasound transducers 1207 and 1205 in a non-tilted orientation perpendicular to the coronal plane, while FIG. 14 illustrates the ultrasound transducers 1207 and 1205 in tilted orientation relative to the perpendicular to the coronal plane, with ultrasound transducer 1205 having a greater degree of tilt. As illustrated in FIG. 14, ultrasound scans have different elevation profiles ($SLICE_{1205}$ and $SLICE_{1207}$) into the breast volume, which can then be compounded in various ways to improve image quality.

Figure 15:
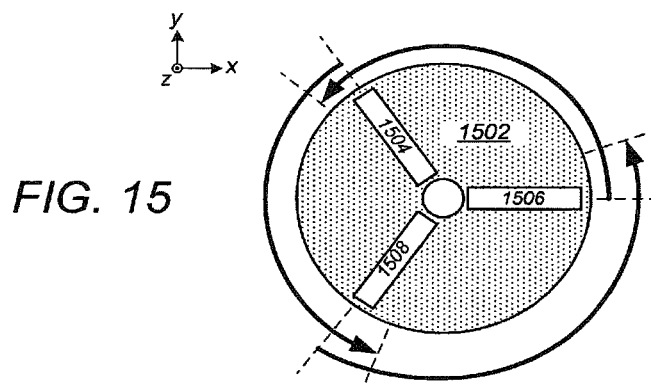
FIG. 15 illustrates a top view of a radial scanning template 1502 according to a preferred embodiment.

FIG. 15 illustrates a top view of a radial scanning template 1502 according to a preferred embodiment, comprising three slot-like openings 1504, 1506, and 1508 corresponding to three ultrasound transducers (not shown). In one preferred embodiment, the radial scanning template 1502 is rotated by 120 degrees plus an overlap angle during the breast ultrasound scan, thereby reducing scanning time as compared to the use of fewer ultrasound transducers. In other preferred embodiments, the radial scanning template 1502 is rotated by the full 360 degrees plus overlap angle and the three (3) resultant scans are compounded in advantageous ways.

Figure 16A:
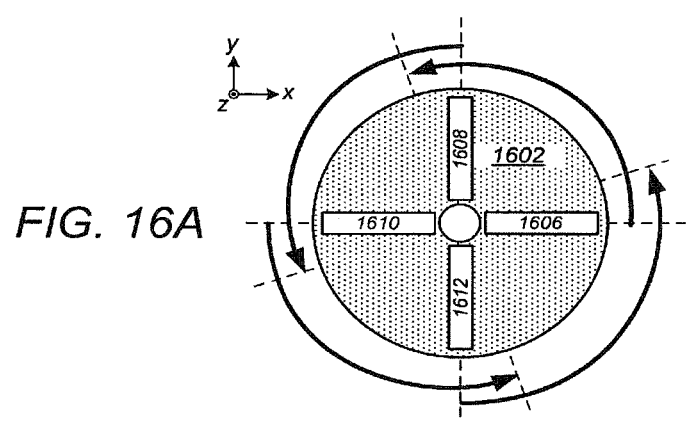
FIG. 16A illustrates a top view of a radial scanning template 1602 according to a preferred embodiment.

FIG. 16A illustrates a top view of a radial scanning template 1602 according to a preferred embodiment, comprising four slot-like openings 1604, 1606, 1608, and 1610 corresponding to four ultrasound transducers (not shown). In one preferred embodiment, the radial scanning template 1602 is rotated by 90 degrees plus an overlap angle during the breast ultrasound scan, thereby reducing scanning time as compared to the use of fewer ultrasound transducers. In other preferred embodiments, the radial scanning template 1602 is rotated by the full 360 degrees plus overlap angle and the four (4) resultant scans are compounded in advantageous ways.

Figure 16B:
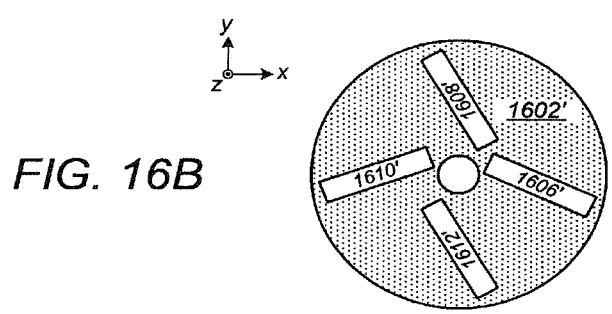
FIG. 16B illustrates a variant of FIG. 16A in which each slot-like opening is skewed relative to a radially-extending line therethrough.

More generally, "N" slot-like openings can be provided and the radial scanning template can be rotated by 360/N degrees plus an overlap angle. Alternatively, the radial scanning template is rotated by the full 360 degrees plus overlap angle and the "N" resultant scans compounded in advantageous ways. FIG. 16B illustrates a variant of FIG. 16A in which each slot-like opening is skewed relative to a radially-extending line therethrough. In another preferred embodiment, a firing sequence of the ultrasound transducers is adjusted such that two or more of them can be fired simultaneously into the breast volume without mutual interference.

Figure 17:
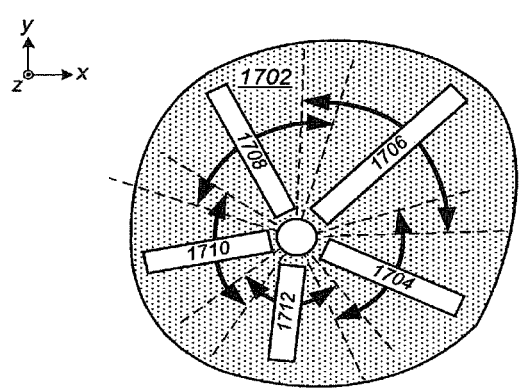
FIG. 17 illustrates a top view of a radial scanning template 1702 according to a preferred embodiment.

FIG. 17 illustrates a top view of a radial scanning template 1702 according to a preferred embodiment, comprising five slot-like openings 1704, 1706, 1708, 1710, and 1712 corresponding to five ultrasound transducers (not shown). According to the preferred embodiment of FIG. 17, at least two of the ultrasound transducers have different lengths corresponding to different vertex-to-base distances around the radial scanning template. Each ultrasound transducer scans a different coronal sector of the breast. In the example of FIG. 17, which is for the left breast of the supine patient, the longest ultrasound transducer 1706 is for scanning the coronal sector nearest the axilla, while the shortest ultrasound transducer 1712 is for scanning an inferior/medial sector of the breast. Accordingly, it is to be appreciated that the general shape of a radial scan template according to the preferred embodiments is not limited to right cone shapes, but rather can have different vertex locations relative to the base. Likewise, a radial scan template according to the preferred embodiments is not limited to circular, planar basis, but rather can have differently-shaped bases (e.g., oblong, elliptical, cam-like), and/or non-planar bases.

Figure 18:
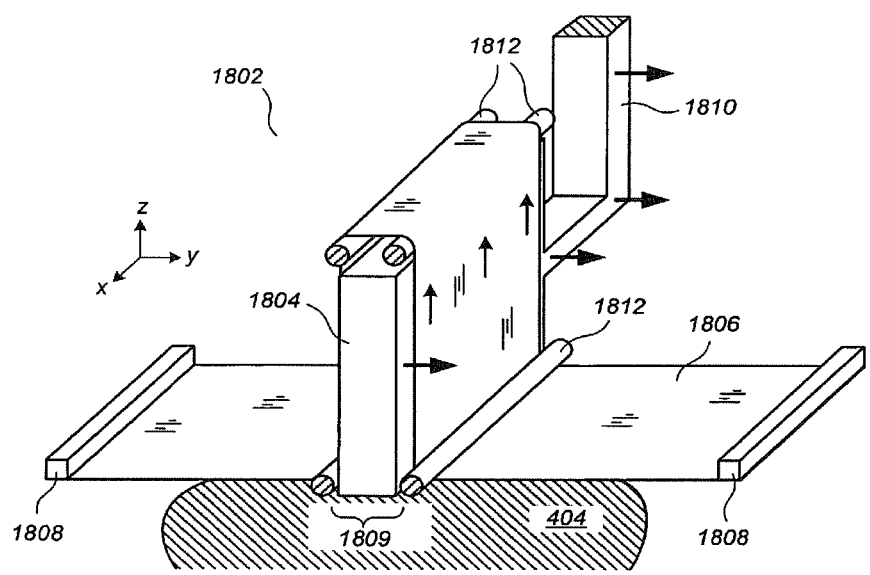
FIG. 18 illustrates a conceptual perspective view of an apparatus for ultrasonically scanning a breast according to a preferred embodiment.

FIG. 18 illustrates a conceptual perspective view of an apparatus for ultrasonically scanning a breast according to a preferred embodiment, comprising an ultrasound transducer 1804 having a scanning surface, and a compressor 1802 having a compressive surface 1806 that compresses a skin surface of the breast 404, wherein a slot-like opening 1809 is formed in the compressive surface 1806 through which the scanning surface of the ultrasound transducer 1804 directly contacts the skin surface. The compressor 1802 is configured such that the slot-like opening 1809 moves laterally over the compressed skin surface in conjunction with the ultrasound transducer 1804. Thus, both breast compression and direct skin contact are advantageously provided during the ultrasound scan. In the example of FIG. 18, the compressive surface 1806 comprises a flexible membrane and a roller assembly 1812 causing the membrane to rise and fall relative to the skin surface, but not to move laterally relative to the skin surface, as the ultrasound transducer 404 is moved laterally across the compressed breast. The ultrasound transducer 1804 is driven from the side by a mechanical arm 1810 to accommodate the movement of the membrane thereover. The membrane can comprise any of the materials discussed supra in relation to the membrane 710 of FIG. 7.

The obtained ultrasound scans can be advantageously used in a variety of ways in accordance with the preferred embodiments. For example, it has been found that the acquired volumetric data is particularly advantageous in generating SOMOGRAM™ representations of the breast, SOMOGRAM™ being a trademark of U-Systems, Inc., of San Jose, Calif. Various compounding schemes for data obtained from transducers having at least one different imaging parameter can be used, including compounding on a per-slice basis, compounding on a per-volume basis, and compounding on a per-SOMOGRAM™ basis.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be appreciated that any of a variety of different frame assemblies can be used that position, compress, rotate, and otherwise manipulate the scanning template, whether the scanning template is permanently used and re-used for different patients or is disposable for each patient, without departing from the scope of the present teachings. Moreover, in one or more alternative preferred embodiments, the basic profile of the radial scanning template can be dome-shaped, ellipsoidally shaped, etc., rather than strictly cone-shaped as indicated in the attached drawings. The scanning surface of the ultrasound transducer can be arced in a similar manner, if desired. Therefore, reference to the details of the embodiments are not intended to limit their scope.

What is claimed is:

1. A full-field breast ultrasound scanning apparatus comprising
   a support arm,
   a breast template generally shaped as a truncated cone having (i) an inside wall surface (ii) a downwardly facing base having a bottom opening, (iii) an upwardly facing vertex having a top opening sized and configured for a patient's breast nipple to protrude through the top opening when the breast of a supine patient is compressed chestwardly with said template, (iv) convergence of the inside wall surface toward the top opening at a convergence angle exceeding 90° by at least several degrees, (v) a slot in the side wall extending outwardly from the vertex, and (vi) a membrane that is permeable to an ultrasound couplant and extends across said slot-like opening,
   an elongated ultrasound transducer shaped and configured to fit in said slot such that the transducer makes physical and acoustic contact with the membrane and is outside the space encircled by the template wall,
   an actuator configured to drive the template and the transducer in a rotational motion about a central axis of the template through a selected angle plus an overlap angle that is in the range of 5° to 45°,
   a connector configured to connect the template, transducer and actuator to the support arm,
   said support arm being configured to move the template and transducer down toward a supine patient to thereby compress a patient's breast chestwardly within the template, with the breast nipple protruding through the top opening of the template, and with the breast contacting the entire inside wall surface of the template, said template having an inside surface that is slippery relative to the compressed breast,
said actuator being selectively actuated to drive the template and the transducer in said rotational motion to thereby rotate the template and the transducer relative to the breast through said selected angle plus overlap angle;
wherein the transducer presses against the breast through said membrane during said rotational motion and is configured to generate a multiplicity of sectional ultrasound views of the breast that are radially oriented relative to the breast;
wherein a scanning surface of the ultrasound transducer has a pattern of a multiplicity of transducer elements extending in the radial direction, and wherein fewer transducer elements fire per unit time nearer said vertex than nearer the base of the template when generating said sectional views; and
wherein a multiplicity of said sectional views are for the same angular orientation of the transducer relative to the breast due to said rotational motion over the selected angle plus overlap angle;
said multiplicity of sectional views for the same angular orientations being blended to reduce discontinuity artifacts in further processing said sectional views into a three-dimensional volume representation of the breast.

2. The full-field breast ultrasound scanning apparatus of claim 1, further including configuring said transducer to carry out beam-steering for facilitating sub-areola imaging of the breast.

3. The full-field breast ultrasound scanning apparatus of claim 1 in which said membrane comprises a taut fabric.

4. The full-field breast ultrasound scanning apparatus of claim 1 in which said membrane comprises a taut polyester chiffon fabric.

5. The full-field breast ultrasound scanning apparatus of claim 1 in which said convergence angle is in the range of 120° to 165°.

* * * * *